United States Patent [19]

Kaplan et al.

[11] Patent Number: 5,431,896

[45] Date of Patent: *Jul. 11, 1995

[54] MICROBIAL IMMUNOREGULANT

[75] Inventors: Louis Kaplan, New City, N.Y.; Robert P. Borris, Glen Gardner, N.J.; Kevin M. Byrne, West Trenton, N.J.; Linda S. Wicker, Westfield, N.J.; Deborah L. Zink, Manalapan, N.J.

[73] Assignee: Merck & Co., Inc., Rahway, N.J.

[*] Notice: The portion of the term of this patent subsequent to Jan. 1, 2008 has been disclaimed.

[21] Appl. No.: 923,025

[22] Filed: Jul. 30, 1992

Related U.S. Application Data

[63] Continuation of Ser. No. 728,814, Jul. 11, 1991, abandoned, which is a continuation of Ser. No. 323,655, Mar. 15, 1989, abandoned.

[51] Int. Cl.$^6$ ............... A61K 35/00; A61K 31/395; C07D 498/16; C07F 7/04
[52] U.S. Cl. .............. 424/0.116; 424/122; 435/75; 435/119; 435/127; 435/128; 435/898; 514/291; 514/23; 540/456; 540/452
[58] Field of Search .......... 424/116, 122; 435/75, 435/119, 127, 128, 898; 514/291, 23; 540/456, 452

[56] References Cited

U.S. PATENT DOCUMENTS

| | | | |
|---|---|---|---|
| 3,244,592 | 4/1966 | Arai | 424/123 |
| 4,894,366 | 1/1990 | Okuhara et al. | 540/456 |
| 4,929,611 | 5/1990 | Okuhara et al. | 540/456 |
| 4,956,352 | 9/1990 | Okuhara et al. | 540/456 |
| 4,975,372 | 12/1990 | Arison et al. | 435/119 |
| 4,981,792 | 1/1991 | Inamine et al. | 435/119 |
| 5,011,844 | 4/1991 | Fehr | 514/291 |
| 5,138,052 | 8/1992 | Chen et al. | 540/456 |
| 5,149,701 | 9/1992 | Shafiee et al. | 540/456 |
| 5,162,334 | 11/1992 | Goulet et al. | 514/291 |

FOREIGN PATENT DOCUMENTS

| | | |
|---|---|---|
| 0184162 | 6/1986 | European Pat. Off. . |
| 0323042 | 7/1989 | European Pat. Off. . |
| 0349061 | 1/1990 | European Pat. Off. . |

OTHER PUBLICATIONS

*The Merck Manual*, 15th edition pp. 322–337 (1987).

*Primary Examiner*—Douglas W. Robinson
*Assistant Examiner*—Elli Peselev
*Attorney, Agent, or Firm*—Mollie M. Yang; David L. Rose

[57] ABSTRACT

Described is a new immunosuppressant, L-687,819, a C-31 demethylated derivative of L-683,795 (FK-523), produced under fermentation conditions utilizing the new mutant microorganism, *Streptomyces hygroscopicus* subsp. *ascomyceticus* (Merck Culture Collection MA 6646) ATCC No. 53855, being a blocked mutant of *Streptomyces hygroscopicus* subsp. *ascomyceticus* (MA 6475) ATCC No. 14891. The macrolide immunosuppressant is useful in preventing human host rejection of foreign organ transplants, e.g. bone marrow and heart transplants.

3 Claims, 3 Drawing Sheets

L-687,819

MICROBIAL IMMUNOREGULANT

This application is a continuation of application Ser. No. 07/728,814, filed on Jul. 11, 1991, now abandoned, which is a continuation of application Ser. No. 07/323,655, filed on Mar. 15, 1989, now abandoned.

BACKGROUND OF THE INVENTION

1. Field of the Invention

This invention relates to a new immunosuppressant agent, L-687,819, produced by the fermentation of the new mutant microorganism *Streptomyces hygroscopicus* subsp. *ascomyceticus* (MA 6646) ATCC No. 53855, being a blocked mutant of *Streptomyces hygroscopicus* subsp. *ascomyceticus* (MA 6475), ATCC No. 14891. The process involves culturing the new microorganism under aerobic fermentation conditions in an aqueous carbohydrate medium containing a nitrogen nutrient.

2. Brief Description of Disclosures in the Art

In 1983, the US FDA licensed cyclosporin, an extremely effective anti-rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage and ulcers which in many cases can be very severe.

EPO Publication NO. 0184162 to Fujisawa, hereby incorporated by reference, describes a new macrolide immunosuppressant FK-506 which is reputed to be 100 times more potent than cyclosporin. The macrolide, as well as the structurally related FK-525, are produced by fermentation of a particular strain of *Streptomyces tsukubaensis*. Also described are the closely related macrolide immunosuppressants, FK-520 and FK-523, produced by *S. hygroscopicus* subsp. *yakushimaensis*.

U.S. Pat. No. 3,244,592 to T. Arai describes the culturing of *Streptomyces hygroscopicus* var. *ascomyceticus* to produce the antifungal "ascomycin".

U.S. Ser. No. 213,025 (case Docket 17767) by S. T. Chen, E. S. Inamine, B. H. Arison, L. S. Wicker, (assigned to Merck & Co. Inc.) hereby incorporated by reference, discloses a new immunosuppressant agent, "demethimmunomycin", L-683,742, a C-31 demethylated analogue of L-683,590 (FK-520) produced by culturing the microorganism Actinoplanacete sp. (MA 6559), ATCC No. 53771, in the presence of L-683,590 to effect a biotransformation of L-683,590.

There is, however, no description in the literature of the production of the immunosuppressive agent L-687,819, being the C-31 demethylated derivative of L-683,795 (FK-523).

New macrolide immunosuppressants in the FK-506 structural family are constantly being searched for in the field.

SUMMARY OF THE INVENTION

It has been found that the immunosuppressant, L-687,819, can be directly obtained by the fermentation of the mutant microorganism *Streptomyces hygroscopicus* subsp. *ascomyceticus* (MA 6646) ATCC No. 53855, derived from ATCC No. 14891 (MA 6475), by mutagenic treatment with N-methyl-N'-nitro-N-nitrosoguanidine. The fermentation does not require the presence of the macrolide immunosuppressant L-683,795 (FK-523), and is conducted under submerged aerobic conditions in an aqueous carbohydrate medium, containing a nitrogen nutrient, said conditions being conducted at a pH below 8.0, e.g., of about 7, for a sufficient time to produce L-687,819, the mono-C-31 demethylated version of L-683,795 (FK-523).

The resultant L-687,819 exhibits immunosuppressive activity, i.e., positive inhibition of T-cell activation, as demonstrated by the calcium ionophore (ionomycin) plus phorbol myristate acetate (PMA) induced T-cell stimulation assay, also referred to herein as the "T-cell proliferation assay". The principle of this assay is to measure the proliferation of mouse T lymphocytes stimulated with the combination of ionomycin plus PMA. A positive sample in this assay will inhibit T-cell proliferation, as indicated by reduced tritiated thymidine uptake.

Figure 1:
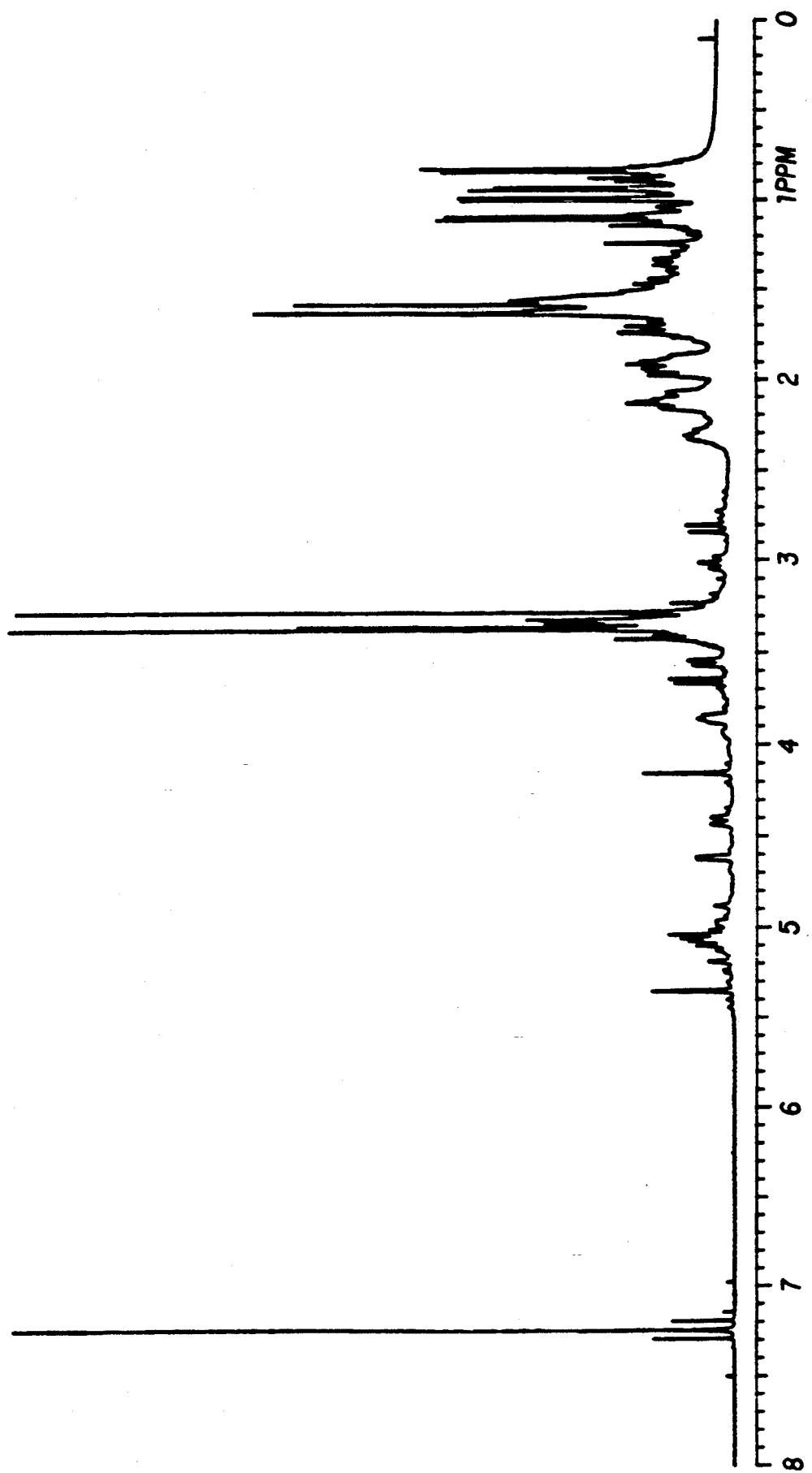
FIG. 1 is a proton ($^1$H) nuclear magnetic resonance (NMR) spectrum of L-687,819 at 400 MHz in CDCl$_3$.

In accordance with this invention, there is provided a new immunosuppressant, identified as L-687,819, having a molecular formula of $C_{41}H_{65}NO_{12}$ (calculated 1051.6088, found 1051.6089 for $C_{41}H_{65}NO_{12}+T_4$, where $T=SiC_3H_8$), as determined by electron impact mass spectrometry and exhibiting a proton nuclear magnetic resonance spectrum as illustrated in FIG. 1, produced by culturing a strain of *Streptomyces hygroscopicus* subsp. *ascomyceticus* (MA 6646) ATCC No. 53855, under submerged aerobic fermentation conditions in an aqueous carbohydrate medium, containing a nitrogen nutrient, for a sufficient time to produce product L-687,819.

DETAILED DESCRIPTION OF THE INVENTION AND PREFERRED EMBODIMENTS

The present invention involves the fermentation of *Streptomyces hygroscopicus* subsp. *ascomyceticus* ATCC No. 53855, to produce L-687,819. The microorganism is currently on restricted deposit filed Jan. 12, 1989, with the American Type Culture Collection, 12301 Parklawn Drive in Rockville, Md. as ATCC No. 53855, and in the Merck Culture Collection in Rahway, N.J. as MA 6646. The physical characteristics and taxonomy, including morphological, cultural, biological and physiological characteristics are briefly described hereinbelow.

STRAIN MA6646

Microscopic observations—Branching filamentous mycelia 0.6 microns in diameter. Sporophores appear as short, compact spirals.

Oat Meal Agar
    Vegetative Growth: Reverse: Greyish-white.
    Aerial Mass: Abundant, matte, grey to black.
    Soluble Pigment: None.

Glycerol-Asparagine
    Vegetative Growth: Reverse: Off-white, translucent. Obverse: Off-white, translucent, erose edge.
    Aerial Mycelium: Sparse, off-white, powdery.
    Soluble Pigment: None.

Inorganic Salts-Starch Agar
 Vegetative Growth: Reverse: cream-yellow.
 Aerial Mass: Abundant, velvety, light grey to black.
 Aerial Mycelium: White, velvety.
 Soluble Pigment: None.
Yeast Extract-Malt Extract Agar
 Vegetative Growth: Reverse: Greyish-yellow.
 Aerial Mass: Abundant, light to medium grey, matte, cottony.
 Soluble Pigment: None.

| Carbohydrate Utilization Pattern | | | | | |
|---|---|---|---|---|---|
| d-glucose | ++ | d-maltose | + | sucrose | − |
| d-arabinose | +/− | d-mannitol | ++ | d-xylose | ++ |
| l-arabinose | +/− | d-mannose | ++ | l-xylose | − |
| d-fructose | ++ | l-mannose | − | alpha d-lactose | ++ |
| l-glucose | − | d-raffinose | − | beta d-lactose | ++ |
| inositol | +/− | l-rhamnose | ++ | | |

Where ++ indicates substantial growth; + indicates moderate growth; +/− indicates trace growth; and − indicates no growth.

The present invention process can be practiced with any "L-687,819-producing" strain of mutant *Streptomyces hygroscopicus* subsp. *ascomyceticus* and particularly preferred is the ATCC No. 53855 strain.

In general, L-687,819 can be produced by culturing (fermenting) the above-described "L-687,819-producing strain" in an aqueous nutrient medium containing sources of assimilable carbon and nitrogen, preferably under submerged aerobic conditions (e.g. shaking culture, submerged culture, etc.). The aqueous medium is preferably maintained at a pH of about 7 at the initiation and termination (harvest) of the fermentation process. A higher pH leads to substantial and/or total loss of product. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described hereinbelow.

The preferred sources of carbon in the nutrient medium are carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As to the conditions for the production of L-687,819 in massive amounts, submerged aerobic cultural conditions are preferred therefor. For the production in small amounts, a shaking or surface culture in a flask, bottle, or culture dish is employed. Furthermore, when the growth is carried out in large tanks, it is preferable to use the vegetative form of the organism for inoculation into the production tanks in order to avoid growth lag in the process of production of L-687,819. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of L-687,819 and is generally autoclaved to sterilize the medium prior to inoculation. The pH of the medium is generally adjusted to about 7.0 prior to the autoclaving step by suitable addition of an acid or base, preferably in the form of a buffering solution.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°–35° C., for a period of about 48 hours to 96 hours, which may be varied according to fermentation conditions and scales. Preferably, the production cultures are incubated for about 96 hours at 27° C. on a rotary shaker operating at 240 rpm, wherein the pH of the fermentation medium is maintained at 7.0 to harvest.

Preferred culturing/production media for carrying out the fermentation include the following media:

| | g/liter |
|---|---|
| Seed Medium A | |
| Glucose | 20.0 |
| Difco Yeast Extract | 20.0 |
| Hycase SF | 20.0 |
| KNO$_3$ | 2.0 |
| FeSO$_4$.7H$_2$O | 0.025 |
| NaCl | 0.5 |
| MgSO$_4$.7H$_2$O | 0.5 |
| MnSO$_4$.7H$_2$O | 0.005 |
| ZnSO$_4$.7H$_2$O | 0.01 |
| CaCl$_2$.2H$_2$O | 0.02 |
| Production Medium B | |
| Glucose | 22 |
| Glycerol | 25 |
| Corn Steep Liquor | 10 |
| Difco Yeast Extract | 15 |
| Lactic Acid | 2 |
| L-Tyrosine | 4 |
| MOPS | 10 |
| CaCO$_3$ | 0.25 |
| Adjust pH to 6.8 | |

The produced L-687,819 can be recovered from the culture medium by conventional means which are commonly used for the recovery of other known biologically active substances. The L-687,819 substance produced is found in the cultured mycelium and filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred method is solvent extraction, particularly using methanol.

Figure 3:
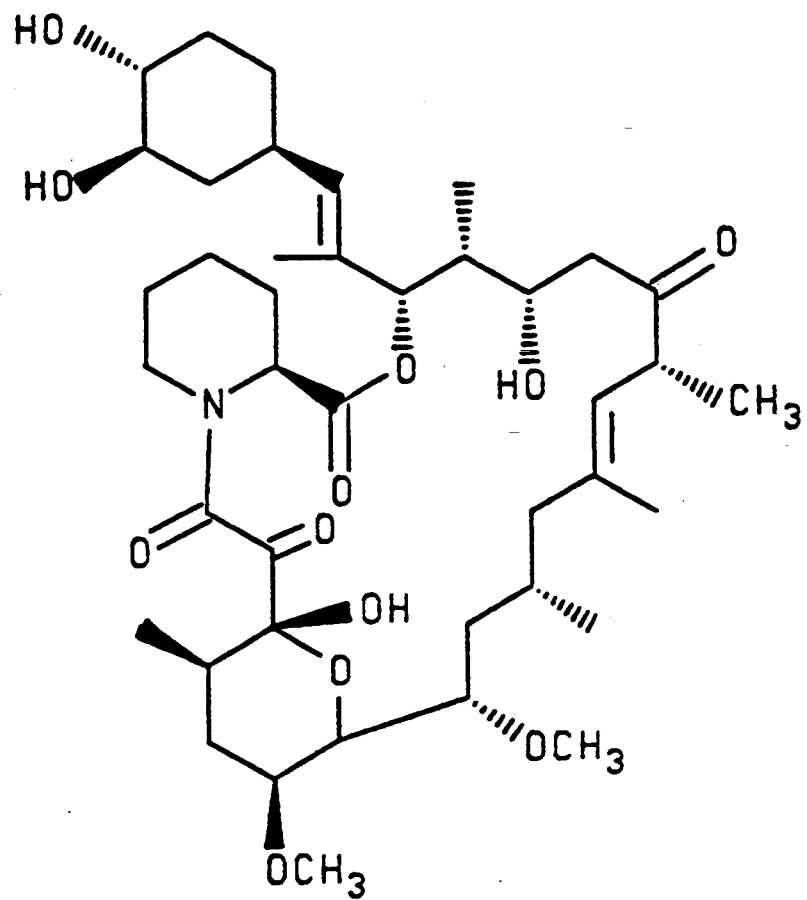
FIG. 3 illustrates the assigned chemical structure for L-687,819 based on the spectral and mass spectrometry evidence.

The product L-687,819 from the fermentation exhibits positive immunosuppressive activity by the "T-cell proliferation assay" and possesses utility on this basis and exhibits the following physical characteristics:
1. White amorphous powder
2. Solubility in methanol
3. Molecular formula of $C_{14}H_{65}NO_{12}$, calculated value of 1051.6088, found 1051.6089, for $C_{41}H_{65}NO_{12}+T_4$, where $T=SiC_3H_8$, as determined by electron impact mass spectrometry which is consistent with the assigned molecular structure in FIG. 3.

The L-687,819 obtained according to the fermentation processes as explained above can be isolated and purified in a conventional manner, for example, extraction, precipitation, fractional crystallization, recrystallization, chromatography, and the like.

Suitable formulations of the material may also include conventional pharmaceutically acceptable biolabile esters of L-687,819, formed via the hydroxy groups on the molecule, such as the acetate.

It is to be noted that in the aforementioned fermentation reactions and the post-treatment of the fermentation mixture therein, the tautomeric and conformational isomer(s) of L-687,819 are also included within the scope of the present invention.

The L-687,819 of the present invention possesses pharmacological activity such as immunosuppressive activity, antimicrobial activity, and the like, and therefore is useful for the treatment and prevention of the transplantation rejection of organs or tissues such as heart, kidney, liver, medulla ossium, skin, etc., graft-versus-host diseases by medulla ossium transplantation, auto-immune diseases such as rheumatoid arthritis, systemic lupus erythematosus, Hashimoto's thyroiditis, multiple sclerosis, myasthenia gravis, type I diabetes, uveitis, and the like.

The pharmaceutical composition of this invention can be used in the form of a pharmaceutical preparation, for example, in solid, semisolid or liquid form, which contains the L-687,819, of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

For applying this composition to a human, it is preferable to apply it by parenteral or enteral administration. While the dosage of therapeutically effective amount of the L-687,819, varies from, and also depends upon the age and condition of each individual patient to be treated, a daily dose (calculated on the basis of a 70 kg man) of about 0.01–1000 mg, preferably 0.1–500 mg and more preferably 0.5–100 mg, of the active ingredient is generally given for treating diseases, and an average single dose of about 0.5 mg, 1 mg, 5 mg, 10 mg, 50 mg, 100 mg, 250 mg and 500 mg is generally administered.

The following examples are given for the purpose of illustrating the present invention and should not be construed as being limitations on the scope or spirit of the instant invention.

EXAMPLE 1

Culture Conditions

The fermentation of MA6646 was carried out by inoculating a 250 ml baffled Erlenmeyer flask containing 44 ml of an autoclaved seed medium consisting of $KNO_3$, 0.2%, HyCase SF, 2%, Difco yeast extract, 2%, glucose, 2% $FeSO_4.7H_2O$ 0.0025%, NaCl, 0.05%, $MgSO_4.7H_2O$, 0.05%, $MnSO_4.7H_2O$, 0.0005%, $ZnSO_4.7H_2O$, 0.001%, and $CaCl_2.2H_2O$, 0.002%. The seed medium was inoculated with MA6646 (ATCC No. 53855) spores from Bennett's medium and incubated for 42–48 hours at 27° C. on a rotary shaker operating at 220 rpm. A 1.0 ml aliquot of the resulting seed culture was used to inoculate a 250 ml non-baffled Erlenmeyer flask containing production medium which consisted of glycerol, 2.5%, glucose, 2.2%, corn steep liquor, 1%, Difco yeast extract, 1.5%, lactic acid, 0.2% (v/v), L-tyrosine, 0.4%, MOPS, 1%, and $CaCO_3$, 0.025% where the pH was adjusted to pH 6.8 with NaOH prior to autoclaving. The production culture was incubated for 96 hours at 27° C. on a rotary shaker operating at 220 rpm. A methanol extraction was achieved by addition of an equal volume of methanol to the broth culture, agitating at high speed on an Eberbach reciprocating shaker for 30 min followed by centrifugation. The aqueous methanolic extracts were analyzed by TLC and HPLC.

By reverse phase HPLC (Whatman Partisil 5 ODS-3, 0.1% aqueous $H_3PO_4:CH_3CN$, 40:60, 1 ml/min), the major component of all isolates had a retention time of 7.79 min having the same retention time by HPLC and the same Rf by TLC as 31-desmethyl-L-683-590 (L-687,819).

A minor component was noticed, at a retention time of 6.98 minutes. The minor component was isolated on a semi-preparative reversed phase octadecyl($C_{18}$)HPLC column (RAININ TM Dynamax C-18 Column). Six shake flask cultures of the mutant were extracted with an equal volume of methanol, centrifuged, and the supernatant evaporated to remove the methanol. The resulting aqueous phase was extracted twice with ethyl acetate and evaporated to dryness under a stream of nitrogen. The residue was resuspended in methanol and a 50 microliter aliquot was injected onto the semi-preparative column. The solvent system was 0.1% aqueous $H_3PO_4:CH_3CN$(50:50) at a flow rate of 4 ml/min. The broad peak eluting at 12.5 min was collected in 1 ml fractions which were adjusted to pH 6.0 with MOPS buffer. A sample was submitted for T-cell proliferation (IL-2) assay and shown to possess immunosuppressive activity.

EXAMPLE 2

Preparative Isolation

A scaleup of the fermentation procedure in Example 1 was carried out to produce a larger quantity of material. The culture solids were removed from 45 liters of fermentation broth by centrifugation. The resulting cake was then extracted twice with methanol (one liter each time). The culture supernatant was extracted with one half volume of ethyl acetate (20 liters), and the resulting ethyl acetate extract pooled with the methanol extract of the culture solids and freed of organic solvent by flash evaporation at reduced pressure to afford an aqueous dispersion. This aqueous dispersion was diluted with distilled water to a final volume of 1.5 liters and extracted with an equal volume of ethyl acetate. The ethyl acetate extract was then washed with distilled water to remove residual water-soluble contaminants. The washed ethyl acetate extract was freed of solvent by flash evaporation at reduced pressure to afford 55.3 grams of a crude active extract.

The crude active extract was chromatographed on a 5 liter column of silica gel (Aldrich Chemical, #24398-1, Grade 62, 60–200 mesh) in hexane:acetone (3:1). After application of the sample, the column was washed with two bed volumes of the same solvent, and then eluted with hexane:acetone (11:9), collecting 2 liter fractions. Fractions 10–14, containing the object compound, were pooled and evaporated under reduced pressure to afford 4.05 grams of richcut. This material was rechromatographed on a 1 liter column of silica gel-60 (E. Merck, #9385, 230–400 mesh) in hexane:acetone (11:9). After application of the sample, the column was eluted with solvent of the same composition at 25 ml/min. Two hundred fifty ml fractions were collected with the richcut eluting in fractions 22–40. These fractions were pooled and evaporated to dryness to afford 2.91 grams of oily residue.

Further purification was achieved by means of preparative reverse-phase high performance liquid chromatography (HPLC). Approximately 100 milligrams of richcut were dissolved in 1 ml of methanol and chromatographed in two parts on a Rainin Dynamax-C18 column, 21.4×250 mm, operating at 60° C., eluted with acetonitrile:water (3:2) at 10 ml/min, with detection of ultraviolet absorbance at 205 nm. Fifteen milliliter fraction were collected throughout the chromatographic separations. Fractions 9–11 from each separation contained the object compound, and were therefore pooled and concentrated to dryness under reduced pressure. The residue was rechromatographed on the same column at 60° C., eluted with acetonitrile:water (1:1) at 10 ml/min. The object compound eluted from 42–48 minutes under these conditions. Evaporation of the heartcut of this peak afforded 2.7 mg of the object compound, in a state of high purity, as a white amorphous solid.

Figure 2:
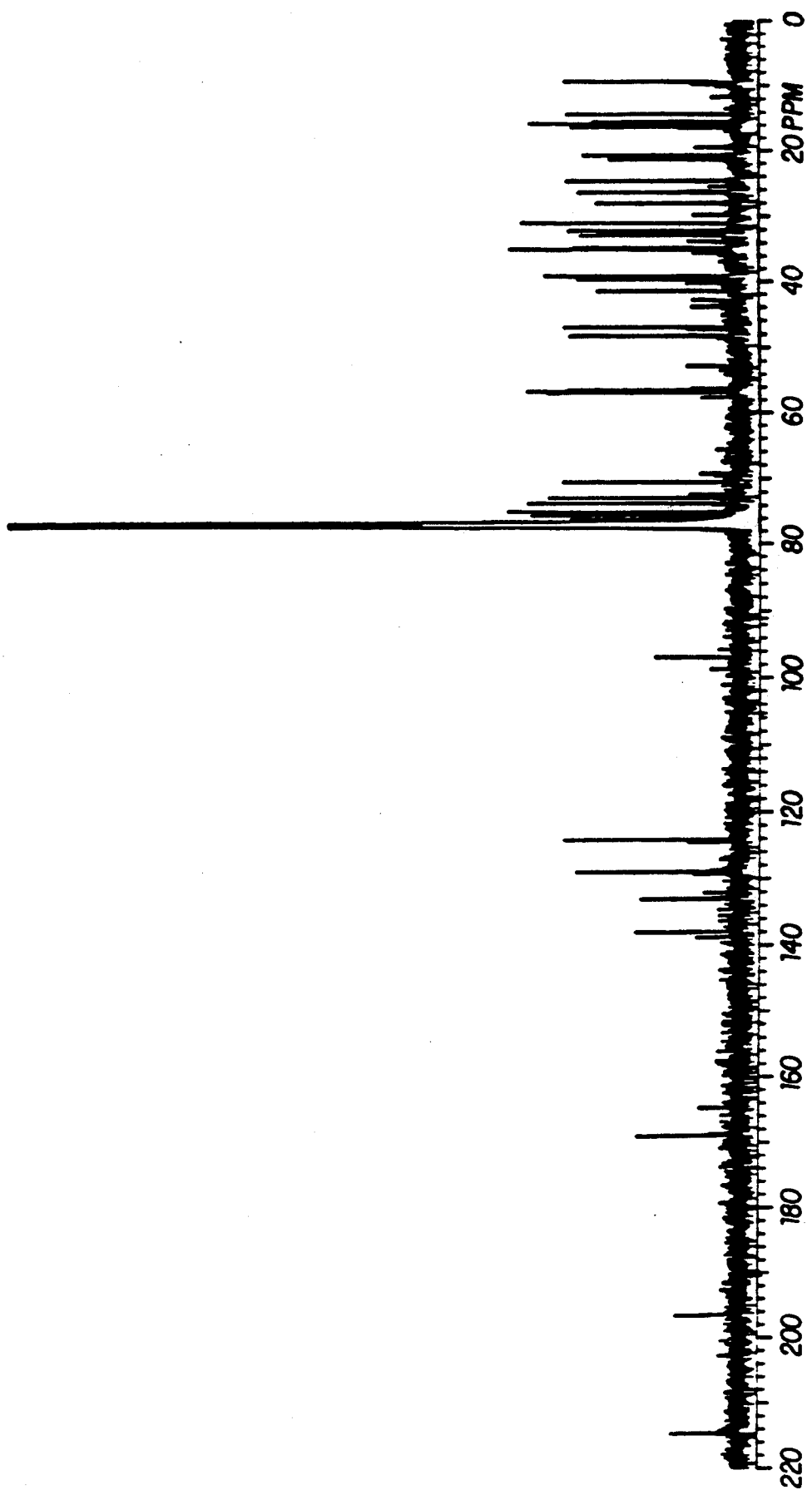
FIG. 2 is a carbon-13 ($^{13}$C) NMR spectrum of L-687,819 at 100 MHz in CDCl$_3$.

The proton NMR spectrum of this product in CDCl$_3$ is shown in FIG. 1, with chemical shifts reported as PPM (delta) relative to tetramethylsilane (TMS=O PPM). Residual solvent protons were employed as the internal standard (7.24 PPM). The carbon-13 NMR spectrum of the product in CDDl$_3$ is shown in FIG. 2, with chemical shifts reported as PPM (delta) relative to tetramethylsilane (TMS=O PPM). The carbon resonance of the solvent was employed as the internal standard (77.0 PPM). High resolution electron impact mass spectrometry of the tetra-(trimethylsilyl)-derivative of the object compound afforded a molecular ion of 1051.6089 ($C_{41}H_{65}NO_{12}+T_4$, where $T=SiC_3H_8$, calculated 1051.6088), and fragmentation consistent with the proposed structure. The purified sample was sent for T-cell proliferation assay (IL-2). The results are listed in Example 3.

EXAMPLE 3

T-Cell Proliferation Assay

1. Sample Preparation

Purified L-687,819, as prepared by HPLC above, was dissolved in absolute ethanol at 1 mg/ml.

2. Assay

Spleens from C57B1/6 mice were taken under sterile conditions and gently dissociated in ice-cold RPMI 1640 culture medium (GIBCO, Grand Island, N.Y.) supplemented with 10% heat-inactivated fetal calf serum (GIBCO). Cells were pelleted by centrifugation at 1500 rpm for 8 minutes. Contaminating red cells were removed by treating the pellet with ammonium chloride lysing buffer (GIBCO) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 250° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5\times10^5$ cells/ml in complete culture medium composed of RPMI 1640 medium with 10% heat-inactivated fetal calf serum, 100 mM glutamine, 1 mM sodium pyruvate, $2\times10^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The control, being the medium without test drug, and various below-indicated dilutions of the sample (above-described L-687,819) to be tested were then added in triplicate wells at 20 μl/well. L-679,934 (FK-506) was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Beta-counter). Mean counts per minute of replicate wells were calculated and the results expressed as percent inhibition of tritiated thymidine uptake (proliferation) as follows:

$$\% \text{ Inhibition} = 100 - \left[ \frac{\text{Mean cpm sample tested}}{\text{Mean cpm control medium}} \times 100 \right]$$

The results of % inhibition at various concentrations of L-687,819 are presented in the following table:

TABLE

Inhibition of T-Cell Proliferation by L-687,819

| L-687,819 (ng/ml) | % Inhibition |
|---|---|
| 100 | 98.8 |
| 10 | 76.1 |
| 6.6 | 51.3 |
| 4.4 | 15.9 |
| 2.9 | 0 |
| 1.3 | 0 |
| 0.58 | 0 |
| 0.26 | 9.1 |
| 0.11 | 9.5 |

Notes:
1. Mouse T cell cultures were pulsed with $^3$H-thymidine for 4 hours prior to harvesting at 48 hours.
2. Standard L-679,934 (10 ng/ml) gave 99% inhibition.
3. IC$_{50}$ = 7.0 ng/ml = 9.17 nM for L-687,819.
4. Inhibition of proliferation was reversed by the addition of 50 units/ml of recombinant human IL-2.

What is claimed is:

1. An immunosuppressant, designated as L-687,819, which exhibits: positive inhibition of T-cell activation by the T-cell proliferation assay, a proton nuclear magnetic resonance spectrum as depicted in FIG. 1, a carbon-13 nuclear magnetic resonance spectrum as depicted in FIG. 2, and a molecular formula of $C_{41}H_{65}NO_{12}$ as determined by electron impact mass spectrometry.

2. A pharmaceutical composition containing a therapeutically effective amount of L-687,819, as defined in claim 1, in combination with a pharmaceutically acceptable, substantially non-toxic carrier or excipient.

3. An immunosuppressant, L-687,819, of the structural formula:

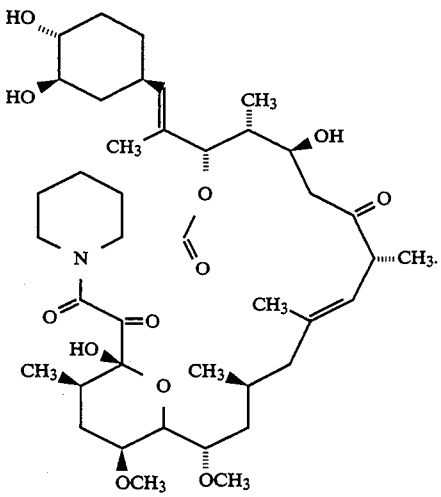

* * * * *